United States Patent
Minato et al.

(10) Patent No.: US 10,624,823 B2
(45) Date of Patent: Apr. 21, 2020

(54) OIL-IN-WATER TYPE EMULSION COSMETIC FOR LIPS

(71) Applicant: SHISEIDO COMPANY, LTD., Tokyo (JP)

(72) Inventors: Ayaka Minato, Yokohama (JP); Noriko Tomita, Yokohama (JP); Yukiko Hiruma, Yokohama (JP); Hiroko Nakata, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/312,833

(22) PCT Filed: Jun. 7, 2017

(86) PCT No.: PCT/JP2017/021106
§ 371 (c)(1),
(2) Date: Dec. 21, 2018

(87) PCT Pub. No.: WO2018/003440
PCT Pub. Date: Jan. 4, 2018

(65) Prior Publication Data
US 2019/0262242 A1     Aug. 29, 2019

(30) Foreign Application Priority Data

Jun. 29, 2016 (JP) ................ 2016-129445

(51) Int. Cl.
| | | |
|---|---|---|
| A61K 8/06 | (2006.01) | |
| A61K 8/81 | (2006.01) | |
| A61K 8/891 | (2006.01) | |
| A61K 8/31 | (2006.01) | |
| A61K 8/03 | (2006.01) | |
| A61K 8/92 | (2006.01) | |
| A61K 8/58 | (2006.01) | |
| A61Q 1/04 | (2006.01) | |
| A61Q 1/06 | (2006.01) | |

(52) U.S. Cl.
CPC ............ *A61K 8/062* (2013.01); *A61K 8/06* (2013.01); *A61K 8/31* (2013.01); *A61K 8/8111* (2013.01); *A61K 8/891* (2013.01); *A61K 8/92* (2013.01); *A61Q 1/04* (2013.01); *A61Q 1/06* (2013.01); *A61K 2800/43* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 2011/0002864 A1 | 1/2011 | Ilekti et al. | |
| 2012/0237467 A1* | 9/2012 | Sasada | A61K 8/31 424/64 |
| 2015/0290114 A1* | 10/2015 | Ikeda | A61K 8/31 514/552 |

FOREIGN PATENT DOCUMENTS

| | | |
|---|---|---|
| JP | 2002-047129 | 2/2002 |
| JP | 2004-168759 | 6/2004 |
| JP | 2011-111443 | 6/2011 |
| JP | 2011-140481 | 7/2011 |
| JP | 2013-136611 | 7/2013 |
| JP | 2013-537214 | 9/2013 |
| WO | WO2014/069403 | 5/2014 |

OTHER PUBLICATIONS

PCT/JP2017/021106, ISR and Written Opinion dated Jul. 11, 2017, 6 pages—Japanese, 2 pages—English.

* cited by examiner

*Primary Examiner* — Sin J Lee
(74) *Attorney, Agent, or Firm* — Andrew F. Young, Esq.; Lackenback Siegel, LLP

(57) ABSTRACT

An oil-in-water emulsion lip cosmetic that is not sticky when applied and superior to provide watery feel, glossy appearance, transparent and long-lasting glossy appearance when applied, comprises (A) an oil phase further comprising (a1) and (a2), wherein (a1) is 5 to 70% by mass of a non-volatile hydrocarbon oil including hydrogenated polyisobutene, and (a2) is 5 to 70% by mass of methylphenyl silicone that separates from (a1) when (a1) and (a2) are mixed with at 25° C.; and (B) an aqueous phase further comprising (b1) and (b2), wherein (b1) is 10 to 80% by mass of an aqueous component, and (b2) is 0.01 to 10% by mass of a colorant.

19 Claims, No Drawings

OIL-IN-WATER TYPE EMULSION COSMETIC FOR LIPS

RELATED APPLICATIONS

This application is a Sec. 371 national phase of and claims priority to Ser. No.: PCT/JP2017/021106 filed Jun. 7, 2017, the entire contents of which are incorporated herein by reference, and which in turn claims the priority of Japanese Patent Application No. 2016-129445 filed on Jun. 29, 2016, which is incorporated herein by reference.

FIELD OF THE INVENTION

The present invention relates to an oil-in-water emulsion lip cosmetic, and in particular, relates to an oil-in-water emulsion lip cosmetic that is not sticky when applied and superior to provide watery feel, glossy appearance, transparent and long-lasting glossy appearance when applied.

BACKGROUND OF THE INVENTION

Conventionally, many oil-based cosmetics have been developed for lip cosmetics that enables providing glossy appearance when applied. On the other hand, when incorporating a colorant into the oils, the transparency of the oils per se is decreased.

Meanwhile, in order to impart watery feel to lips, oil-in-water emulsion lip cosmetics have also been developed. For example, it is known that a cosmetic composition comprising water, alkyl cellulose, $C_{10}$-$C_{26}$ alcohol, a certain ester, non-volatile oil, and a stabilizing agent provides such effects (Patent document 1). Whereas, such a cosmetic composition has a drawback in which glossy appearance of lips is not long-lasting along with losing (evaporating) the aqueous components.

Patent literature 1: Japanese unexamined patent publication No. 2013-537214

DISCLOSURE OF THE INVENTION

Problem to be Solved by the Invention

The present invention was made in view of the above-described conventional art. An object of the invention is to provide an oil-in-water emulsion lip cosmetic that is not sticky when applied and superior to provide watery feel, glossy appearance, transparent and long-lasting glossy appearance when applied.

Means to Solve the Problem

As a result of the present inventors' earnest study to solve the problems, it has been found that oil-in-water emulsion lip cosmetics, which are not sticky when applied and superior to provide watery feel, glossy appearance, transparent and long-lasting glossy appearance when applied, are obtained by emulsifying an oil phase comprising a (a1) non-volatile hydrocarbon oil comprising hydrogenated polyisobutene and a (a2) methylphenyl silicone which separates from the (a1) when mixed with the (a1) at 25° C.; and an aqueous phase comprising a (b1) aqueous component and a (b2) colorant. Based on the findings the present invention has been completed.

Specifically, the oil-in-water emulsion lip cosmetic, according to the aspect of the present invention, comprises the following components (A) and (B); wherein (A) an oil phase comprises 5 to 70% by mass of the (a1) non-volatile hydrocarbon oil comprising hydrogenated polyisobutene, and 5 to 70% by mass of (a2) methylphenyl silicone, which separates from (a1) when mixed with (a1) at 25° C.; and (B) an aqueous phase comprises 10 to 80% by mass of the (b1) aqueous component, and 0.01 to 10% by mass of the (b2) colorant.

It is preferable that the above lip cosmetic comprises an (a3) oil-soluble thickener in the (A) oil phase, in which the blending quantity of the thicker is 1% by mass or less based on the lip cosmetic, more preferably, the blending quantity thereof is less than 0.1%, and most preferably none.

It is preferable that the non-volatile hydrocarbon oil according to the above lip cosmetic comprises of 15% by mass or more of the hydrogenated polyisobutene, more preferably 40% by mass thereof and most preferably 55% by mass thereof.

It is preferable that the (a2) methylphenyl silicone according to the above lip cosmetic is diphenyl dimethicone or trimethyl pentaphenyl trisiloxane.

It is preferable that the (b2) colorant according to the above lip cosmetic comprises a water-soluble dye.

It is preferable that the above lip cosmetic comprises a hydrophilic polymer or hydrophilic surfactant and the (b2) colorant comprises an organic pigment.

Effect of the Invention

An oil-in-water emulsion lip cosmetic that is not sticky when applied and superior to provide watery feel, glossy appearance, transparent and long-lasting glossy appearance when applied is obtained by emulsifying an oil phase comprising a (a1) non-volatile hydrocarbon oil comprising hydrogenated polyisobutene and (a2) methylphenyl silicone which separates from (a1) when mixed with (a1) at 25° C.; and an aqueous phase comprising an (b1) aqueous component and a (b2) colorant.

BEST MODE FOR CARRYING OUT THE INVENTION ((A) Oil Phase)

The (A) oil phase comprises a specific amount of the (a1) non-volatile hydrocarbon oil comprising hydrogenated polyisobutene and a specific amount of the (a2) methylphenyl silicone which separates from the (a1) when mixed with the (a1) at 25° C.

The (a1) non-volatile hydrocarbon oil is an oil which closely adheres (coheres) to the lips and imparts glossy appearance to the lips after the (b1) aqueous component evaporates from the lip cosmetic applied to the lips.

It is mandatory that the non-volatile hydrocarbon oil comprises hydrogenated polyisobutene.

The blending quantity of the hydrogenated polyisobutene is preferably 15% by mass or more relative to the total amount of the non-volatile hydrocarbon oil, more preferably 40% by mass or more thereof and most preferably 55% by mass or more thereof. If the blending quantity of hydrogenated polyisobutene in the non-volatile hydrocarbon oil is too small, the adhesion thereof may be poor.

Examples of non-volatile hydrocarbon oils other than hydrogenated polyisobutene include polybutene, polyisobutylene, polyisoprene, liquid paraffin, squalane, hydrogenated polydecene, vaseline, polyethylene wax, and microcrystalline wax.

As non-volatile hydrocarbon oils other than hydrogenated polyisobutene, liquid non-volatile hydrocarbon oils are preferred. Moreover, the viscosity of liquid non-volatile hydrocarbon oil is preferably 10,000 to 100,000 mPa·s. If the viscosity is less than 10,000 mPa·s, the adhesion thereof may be poor. If the viscosity is more than 100,000 mPa·s, the application texture may be heavier.

It is necessary that the blending quantity of (a1) non-volatile hydrocarbon oil is in the range of 5 to 70% by mass relative to the total amount of the cosmetic. In addition, it is preferably 10% by mass or more and more preferably 15% by mass or more.

If the blending quantity of the (a) component is less than 5% by mass, the adhesion thereof may be poor and the gloss persistence thereof may be lower. Moreover, it is preferably 65% by mass or less and if the amount is more than 70% by mass, a stickiness thereof may occur.

It is necessary that (a2) methylphenyl silicone separates from the (a1) when mixed with the (a1) at 25° C. The (a2) component, separates from the (a1) component after the (b1) aqueous component evaporates from the lip cosmetic applied to the lips, and forms a surface layer to reduce sticky feel as well as to maintain glossy finish.

Here, the presence or absence of "separation" was measured under the following conditions.
(Measurement condition)

(a1) and (a2) were used in the ratio ((a1):(a2)=1:1 (mass ratio)) and heated to 90° C. and mixed with stirring and left to stand until reach 25° C. When the boundary was uniformly separated into two layers, it was denoted "separated". When it was a translucent state or a transparently miscible state without a boundary, it was denoted "not separated".

When two kinds or more of methyl phenyl silicones are used as the component (a2), the presence or absence of separation depends upon their blending ratio. Therefore, it is necessary to check the presence or absence of separation in light of the blending ratio of the component (a2).

Examples of methyl phenyl silicone include diphenyl dimethicone, trimethyl pentaphenyl trisiloxane, diphenylsiloxy phenyl trimethicone, and phenyl trimethicone. Among them, it is preferable to comprise diphenyl dimethicone or trimethyl pentaphenyl trisiloxane.

Additionally, these methylphenyl silicones may be incorporated in proportions so as to meet the separation conditions above as the whole (a2) component.

After the lip cosmetic of the present invention is applied to the lips, the (b2) component in the outer layer (B) colors the lips, while the (b1) component evaporates. Then, by shearing between the lip cosmetic and the lips, the (a1) component and (a2) component immediately separate out, the (a1) components closely adheres to the lips, and the (a2) component separates out as a surface layer, therefore, the cosmetic exerts a transfer-resistant property and a long-lasting gloss effect. When such a lip cosmetic sticks to a material, only usually transparent component (a2) sticks to the material. Therefore, the lip cosmetic of the present invention can attain the long-lasting gloss effect for a long time.

It is necessary that the blending quantity of (a2) methylphenyl silicone which separates out when mixed with the (a1) at 25° C. is 5 to 70% by mass relative to the total amount of the cosmetic. It is preferably 10% by mass or more and more preferably 15% by mass or more.

If the blending quantity of the (a2) component is less than 5% by mass, it may cause poor separation upon application, by which exerting long-lasting gloss effect of the cosmetic may be lost. Moreover, it is preferably 65% by mass or less, and if the blending quantity of the (a2) component is more than 70% by mass, the blending quantity of the (a1) component is too small, so that the adhesion to the lips may be poor and the exerting long-lasting gloss effect of the cosmetic may be lost.

Even if any oil other than the (a1) and (a2) is mixed in an amount within a certain range, the phase separation state of the composition is maintained in the temperature range for application. Therefore, an oil compatible with hydrogenated polyisobutene can be blended at an amount within a certain range where the phase separation state can be maintained, and the long-lasting gloss effect is not damaged. Preferably, in terms of close adhesion and long-lasting gloss effect, the amount is preferably 40% by mass or less and more preferably 20% by mass or less, relative to the total mass of the (A) phase.

As such an oil, any oil commonly used in lip cosmetics can be used. Examples include glyceryl diisostearate, trimethylolpropane tri-2-ethyl isostearate, isopropyl myristate, cetyl-2-ethylhexanoate, glyceryl triisostearate, 2-heptyl undecyl palmitate, methyl polysiloxane, glyceryl triisostearate, diisostearyl malate, di(phytosteryl/octyldodecyl) lauroyl glutamate, (phytosteryl/behenyl) dimer dilinoleate, cyclopentasiloxane, isododecane, pentaerythrityl tetraethylhexanoate, triethylhexanoin, trimethylolpropane triethyl hexanoate, triisostearin, carnauba wax, *Oryza sativa* (rice) bran wax, *Euphorbia cerifera* (candelilla) wax. From them, one or more oils may be optionally chosen.

A (a3) oil-soluble thickener is a component used in common oil-based lip cosmetics as a stabilizer. However, in oil-in-water emulsion lip cosmetics according to the present invention, when incorporating the (a3) oil-soluble thickener, the amount of incorporation is preferably 1% by mass or less, more preferably less than 0.1% by mass, relative to the total mass of the cosmetic, and particularly preferably not blended. When the (a3) component is blended, the (a1) component and the (a2) component may not separate out well and the long-lasting gloss effect may not be exerted.

Examples of oil-soluble thickeners include dextrin fatty acid esters such as dextrin palmitate, dextrin myristate, and dextrin (palmitate/ethyl hexanoate), alkyl cellulose such as ethyl cellulose, and glyceryl (behenate/eicosanedioate).
((B) Water Phase)

The (B) aqueous phase is required to contain a certain amount of the (b1) aqueous component and a certain amount of the (b2) colorant.

(b1) aqueous component as long as it can be normally blended for cosmetics can be blended.

Examples of (b1) aqueous components include water, water swellable thickener, moisturizing agent, preservative agent, dispersant, pH adjuster, and antifoaming agent.

It is necessary that the blending quantity of (b1) aqueous component is 10 to 80% by mass relative to the total amount of the cosmetic. It is preferably 15% by mass or more. If the blending quantity of the (b1) component is less than 10% by mass, it may cause poor application texture, such as watery feel, or it may become difficult to incorporate the (b2) colorant. Moreover, it is preferably 60% by mass or less. If the amount is more than 80% by mass, it may cause poor gloss because the amount of the (A) oil phase is too small.

Since the (b2) colorant blended into the oil phase will impair transparency of the oil phase, in the invention of the present application, it is required to incorporate the (b2) colorant into the aqueous phase. If the (b2) colorant is blended into the oil phase, the transparency of the oil phase tends to decrease and a color difference in appearance before and after application of the cosmetic tends to increase.

Examples of (b2) colorants include water-soluble dye, inorganic pigment, and organic pigment.

Examples of water-soluble dyes include Red No. 227, Yellow No. 4, Yellow No. 5, Blue No. 1, and Red No. 230(1).

Examples of inorganic pigments include inorganic powders (for example, talc, kaolin, mica, sericite, muscovite, biotite, phlogopite, synthetic mica, silica, zeolite, barium sulfate, firing calcium sulfate, calcined gypsum, calcium phosphate, fluorine-apatite, hydroxy apatite, and ceramic powder), inorganic white pigments (for example, titanium dioxide and zinc oxide); inorganic red pigments (for example, iron oxide (red iron oxide) and iron titanate); inorganic brown pigments (for example, gamma-iron oxide); inorganic yellow pigments (for example, yellow iron oxide and loess); inorganic black pigments (for example, black iron oxide, carbon, and low oxides of titanium); inorganic purple pigments (for example, mango violet, cobalt violet); inorganic green pigments (for example, chromium oxide, chromium hydroxide, and cobalt titanate); inorganic blue pigments (for example, ultramarine blue and Berlin blue); and pearl pigments (for example, titanium oxide coated mica, titanium oxide coated bismuth oxychloride, titanium oxide coated talc, coloration titanium oxide coated mica, bismuth oxychloride, fish scale flakes).

Examples of organic pigments include zirconium/barium/aluminium lakes such as Red No. 202, Red No. 205, Red No. 220, Red No. 228, Red No. 405, Orange No. 203, Orange No. 204, Yellow No. 205, Yellow No. 401, Blue No. 404, Red No. 3, Red No. 104, Red No. 227, Red No. 401, Orange No. 205, Yellow No. 4, Yellow No. 202, Green No. 3, and Blue No. 1.

When incorporating an organic pigment as the (b2) colorant, it is necessary to incorporate, as dispersant, a hydrophilic polymer or hydrophilic surfactant. In the absence of a dispersant, the organic pigment cannot be successfully blended into the aqueous phase.

Examples of hydrophilic polymers include hydroxypropyl cellulose, hydroxypropyl methylcellulose, hydroxyethyl cellulose, polyvinylalcohol, and polyvinylpyrrolidone.

Examples of hydrophilic surfactants include polysorbate 20, polysorbate 60, polysorbate 80, PEG-40 stearate, PEG-55 stearate, beheneth-10, beheneth-20, and beheneth-30.

Among these dispersants, polyvinylalcohol, polysorbate 60, beheneth-20, and PEG-55 stearate are preferably blended.

It is necessary that the blending quantity of (b2) colorant is 0.01 to 10% by mass relative to the total amount of the cosmetic. It is preferably 0.1% by mass or more. If the blending quantity of the (b2) component is less than 0.01% by mass, coloring of the lips may not be enough or a color difference in appearance before and after application of the cosmetic may increase. Moreover it is preferably 5% by mass or less. If the blending quantity of the (b2) component exceeds 10% by mass, watery feel may poor.

Preferably, besides the (b1) component and the (b2) component, a higher alcohol, is blended into the aqueous phase of the oil-in-water emulsion lip cosmetic of the present invention, since the incorporation enhances stability of the cosmetic. In an oil-in-water cosmetic, a higher alcohol is generally added into an oil phase. However, in the oil-in-water emulsion lip cosmetic of the present invention, if a higher alcohol is added into the oil phase, an excellent long-lasting gloss effect is not obtained.

The higher alcohol is a monovalent alcohol having 6 carbon atoms or more. Among them, a monovalent alcohol having 12 carbon atoms or more is preferably blended. Specific examples include behenyl alcohol, cetyl alcohol, and stearyl alcohol.

The blending quantity of the higher alcohol is preferably 0.1 to 3% by mass relative to the total amount of the cosmetic. Moreover it is more preferably 0.5% by mass or more. If the blending quantity of the higher alcohol is too small, a stabilizing effect due to the incorporation may not be obtained. Moreover it is more preferably 2% by mass or less. If the blending quantity of the higher alcohol is too large, watery feel may poor.

Besides the (A) and (B) components, examples of a surfactant to be preferably blended include surfactants having an HLB value of 4 or more which make only a small influence on phase separation of the oily phase.

Examples of surfactants having an HLB value of 4 or more include polysorbate 60, polyoxyethylene behenyl ether, sucrose fatty acid ester, polysorbate 20, polysorbate 80, PEG-40 stearate, PEG-55 stearate, beheneth-10, beheneth-20, beheneth-30, sorbitan monostearate, glyceryl stearate (SE), sorbitan sesquiisostearate, PEG-5 glyceryl stearate.

The blending quantity of the surfactant is preferably 1 to 10% by mass relative to the total amount of the cosmetic. Moreover, it is more preferably 2% by mass or more. If the blending quantity of the surfactants is too small, successful emulsification may not occur. Moreover, it is more preferably 8% by mass or less. If the blending quantity of the surfactant is too large, watery feel may poor.

The oil-in-water emulsion lip cosmetics of the present invention can be applied to liquid lipsticks such as lip glosses, solid lipsticks, lip essence or serum products, lip concealers, and the like.

EXAMPLES

The present invention will be further described in the following examples. However, the invention is not limited by these examples. In the below examples, unless otherwise specified, the blending quantity of each component will be expressed in % by mass.

At first, the evaluation methods used in the present invention will be explained.

Evaluation (1): Separability

Oils were heated to 90° C. and mixed by stirring. Then, the resulting oil mixture was allowed to stand to 25° C. and after a certain time period, the mixing state of the oils was evaluated based on the evaluation criteria below:
(Evaluation Criteria)
A: Separated into 2 layers with a clear boundary.
B: Separated into 2 layers with a vague boundary.
C: Completely dissolved state with no boundary.
Evaluation (2): Application Texture (Transparency, Watery Feel, Non-Sticky Feel, and Gloss)

20 expert panelists applied the sample to their lips and evaluated the transparency, watery feel, non-sticky feel, and gloss immediately after application.
(Evaluation Criteria)
S 15 or more out of 20 expert panelists made an evaluation that the sample is excellent in application texture.
A: 10 or more and less than 15 out of 20 expert panelists made an evaluation that the sample is excellent in application texture.
B: 5 or more and less than 10 out of 20 expert panelists made an evaluation that the sample is excellent in application texture.
C: Less than 5 out of 20 expert panelists made an evaluation that the sample is excellent in application texture.

Evaluation (3): Long-Lasting Gloss Effect 20 expert panelists applied the sample to their lips and evaluated the long-lasting gloss effect 2 hours after application.
(Evaluation criteria)
S 15 or more out of 20 expert panelists made an evaluation that the sample has long-lasting gloss effect.
A: 10 or more and less than 15 out of 20 expert panelists made an evaluation that the sample has long-lasting gloss effect.
B: 5 or more and less than 10 out of 20 expert panelists made an evaluation that the sample has long-lasting gloss effect.
C: Less than 5 out of 20 expert panelists made an evaluation that the sample has long-lasting gloss effect.
Evaluation (4): Stability at High Temperatures Samples were stored in a thermostatically controlled cabinet at 50° C. for 4 weeks, and evaluated for abnormal changes, including separation.
A: No separation or other changes are observed.
B: Some oil floating/separated-out water is observed.
C: Lots of oil floating/separated-out water is observed.
Evaluation (5): Color Difference Between the Appearance of the Sample and the Lips after Application 20 expert panelists applied a sample to their lips and comparatively evaluated the color of the appearance of the sample and the color of the lips after application.
A: 15 or more out of 20 expert panelists have made an evaluation that there is no color difference between the appearance of the sample and the lips after application.
C: Less than 15 out of 20 expert panelists have made an evaluation that there is no color difference between the appearance of the sample and the lips after application.

Although oil-in-water emulsion cosmetics have more watery feel than oil-based cosmetics, the amount of oil phase that can be blended into them will be smaller. Therefore, to use them as lip cosmetics, types of the oily components for imparting gloss to the lips were examined.

The present inventors evaluated each sample shown in Table 1 below by the evaluation methods (1) to (3) described above. The results are shown in Table 1.

TABLE 1

| | Test Example | | | | | | | | | |
|---|---|---|---|---|---|---|---|---|---|---|
| | 1-1 | 1-2 | 1-3 | 1-4 | 1-5 | 1-6 | 1-7 | 1-8 | 1-9 | 1-10 |
| Octyl dodecanol (*1) | 100 | — | — | — | — | 70 | 80 | 56 | — | — |
| Hydrogenated polyisobutene (*2) | — | 100 | — | — | — | — | — | — | 70 | 70 |
| Diphenyl dimethicone (*3) | — | — | 100 | — | — | — | — | — | 30 | — |
| Trimethyl pentaphenyl trisiloxane (*4) | — | — | — | 100 | — | — | — | — | — | 30 |
| Trimethyl siloxyphenyl dimethicone (*5) | — | — | — | — | 100 | 30 | — | 30 | — | — |
| Ethyl cellulose (*6) | — | — | — | — | — | — | 20 | 14 | — | — |
| Separability | — | — | — | — | — | C | — | C | A | A |
| Transparency | S | S | S | S | S | S | B | A | S | S |
| Non-sticky feel | A | C | A | A | A | A | C | B | A | A |
| Gloss | B | S | A | A | B | B | S | S | S | S |
| Long-lasting gloss effect | C | A | B | B | C | C | A | B | S | S |

(*1): NJ COL 200A (manufactured by New Japan Chemical Co., Ltd.)
(*2): Deodorizing polybutene P (manufactured by NIKKO RICA CORPORATION)
(*3): KF-54 (manufactured by Shin-Ctsu Chemical Co., Ltd.)
(*4): DOW CORNING® PH-1555 HRI COSMETIC FLUID (manufactured by Dow Corning Toray Co., Ltd.)
(*5): BELSIL PDM 20 (manufactured by wacker asahikasei silicone co.ltd.)
(*6): AQUALON N22 0100 ethylcellulose (manufactured by Ashland.)

As shown in Table 1, application texture differed depending on the types of oily components.

When mixing an alcohol, which is a non-volatile hydrocarbon oil, with a silicone oil and/or oily thickener (ethylcellulose), depending on their combination, it was found that some examples (Test Examples 1-6 and 1-8) showed less separability, some examples (Test Examples 1-6, 1-8, etc.) showed less gloss, and that an example (Test Example 1-8) was poor in non-sticky feel.

However, in a combination of hydrogenated polyisobutene, which is a non-volatile hydrocarbon oil, with diphenyl dimethicone or trimethyl pentaphenyl trisiloxane, examples (Test Examples 1-9 and 1-10) were excellent in separability and application texture.

Accordingly it is necessary that the oil phase of oil-in-water emulsion lip cosmetic of the present invention comprises a (a1) non-volatile hydrocarbon oil containing hydrogenated polyisobutene and (a2) methylphenyl silicone which separates out when mixed with (a1) at 25° C.

Next, the influence of the blending quantity of the (a1) component as an aqueous component, the non-volatile hydrocarbon oil (b1), or the methylphenyl silicone (b2) on application texture and long-lasting gloss effect was examined.

The present inventors prepared each sample (liquid lipstick) shown in Tables 2 and 3 below in a usual manner and evaluated them by the evaluation methods (2) and (3) described above. The results are shown in Tables 2 and 3.

TABLE 2

| | Test Example | | | | | | |
|---|---|---|---|---|---|---|---|
| | 2-1 | 2-2 | 2-3 | 2-4 | 2-5 | 2-6 | 2-7 |
| Hydrogenated polyisobutene (*2) | 2.5 | 5 | 15 | 25 | 37.5 | 40 | 42.5 |
| Diphenyl dimethicone (*3) | 2.5 | 5 | 15 | 25 | 37.5 | 40 | 42.5 |
| Ion exchanged water | 85 | 80 | 60 | 40 | 15 | 10 | 5 |

TABLE 2-continued

| | Test Example | | | | | | |
|---|---|---|---|---|---|---|---|
| | 2-1 | 2-2 | 2-3 | 2-4 | 2-5 | 2-6 | 2-7 |
| Sucrose fatty acid ester (*7) | 3.5 | 3.5 | 3.5 | 3.5 | 3.5 | 3.5 | 3.5 |
| Sorbitan monostearate (*8) | 0.5 | 0.5 | 0.5 | 0.5 | 0.5 | 0.5 | 0.5 |
| Polyvinyl alcohol (*9) | 0.5 | 0.5 | 0.5 | 0.5 | 0.5 | 0.5 | 0.5 |
| Red No. 202 (*10) | 0.5 | 0.5 | 0.5 | 0.5 | 0.5 | 0.5 | 0.5 |
| Dipropylene glycol (*11) | 5 | 5 | 5 | 5 | 5 | 5 | 5 |
| Watery feel | S | S | S | S | S | A | C |
| Non-sticky feel | S | S | S | S | S | S | S |
| Gloss | B | A | S | S | S | S | S |
| Long-lasting gloss effect | B | A | A | S | S | S | S |

(*7): DK ESTER S-160N (manufactured by DKS Co. Ltd.)
(*8): NIKKOL SS-10V (manufactured by NIPPON SURFACTANT INDUSTRIES CO., LTD.)
(*9): P.V.A EG-40 (manufactured by The Nippon Synthetic Chemical Industry Co., Ltd.)
(*10): D&C RED #7 CA LAKE C19-011 (manufactured by Sun Chemical Corporation)
(*11): DIPROPYLENE GLYCOL (manufactured by Seiko & Co)

TABLE 3

| | Test Example | | | | | | | |
|---|---|---|---|---|---|---|---|---|
| | 2-8 | 2-9 | 2-10 | 2-11 | 2-12 | 2-13 | 2-14 | 2-15 |
| Hydrogenated polyisobutene (*2) | 75 | 70 | 65 | 60 | 15 | 10 | 5 | — |
| Diphenyl dimethicone (*3) | — | 5 | 10 | 15 | 60 | 65 | 70 | 75 |
| Ion exchanged water | 15 | 15 | 15 | 15 | 15 | 15 | 15 | 15 |
| Sucrose fatty acid ester (*7) | 3.5 | 3.5 | 3.5 | 3.5 | 3.5 | 3.5 | 3.5 | 3.5 |
| Sorbitan monostearate (*8) | 0.5 | 0.5 | 0.5 | 0.5 | 0.5 | 0.5 | 0.5 | 0.5 |
| Polyvinyl alcohol (*9) | 0.5 | 0.5 | 0.5 | 0.5 | 0.5 | 0.5 | 0.5 | 0.5 |
| Red No. 202 (*10) | 0.5 | 0.5 | 0.5 | 0.5 | 0.5 | 0.5 | 0.5 | 0.5 |
| Dipropylene glycol (*11) | 5 | 5 | 5 | 5 | 5 | 5 | 5 | 5 |
| Watery feel | S | S | S | S | S | S | S | S |
| Non-sticky feel | C | A | S | S | S | S | S | S |
| Gloss | S | S | S | S | S | A | A | A |
| Long-lasting gloss effect | B | A | A | S | S | S | A | B |

Depending on the blending quantity of the aqueous component, non-volatile hydrocarbon oil, or methylphenyl silicone, a difference was observed in gloss, long-lasting gloss effect, watery feel, or non-sticky feel. It was found that only when these components were combined under optimum conditions, the samples were excellent in watery feel, non-sticky feel, gloss and gloss persistence.

Based on the above results, it was found that the amount of the aqueous component is required to be 10 to 80% by mass, and preferably 15% by mass or more and preferably 60% by mass or less. It was also found that the amount of the non-volatile hydrocarbon oil is required to be 5 to 70% by mass, preferably 10 to 65% by mass, and more preferably 15 to 65% by mass relative to the total amount of the cosmetic. It was also found that the amount of the methylphenyl silicone is required to be 5 to 70% by mass, preferably 10 to 65% by mass, and more preferably 15 to 65% by mass relative to the total amount of the cosmetic.

Next, the influence of the blending quantity of hydrogenated polyisobutene in the non-volatile hydrocarbon oil on application texture or long-lasting gloss effect was examined.

The present inventors evaluated each sample shown in Tables 4 and 5 below by the evaluation methods (1) to (3) described above. The results are shown in Tables 4 and 5.

TABLE 4

| | Test Example | | | | | | | | |
|---|---|---|---|---|---|---|---|---|---|
| | 1-9 | 3-1 | 3-2 | 3-3 | 3-4 | 3-5 | 3-6 | 3-7 | 3-8 |
| Hydrogenated polyisobutene (*2) | 70 | 38.5 | 28 | 10 | — | 38.5 | 28 | 10 | — |
| Liquid paraffin (*12) | — | 31.5 | 42 | 55 | 70 | — | — | — | — |
| α-olefin oligomer (*13) | — | — | — | — | — | 31.5 | 42 | 55 | 70 |
| Diphenyl dimethicone (*3) | 30 | 30 | 30 | 30 | 30 | 30 | 30 | 30 | 30 |
| Ratio of hydrogenated polyisobutene in the non-volatile hydrocarbon oil | 100 | 55 | 40 | 15 | 0 | 55 | 40 | 15 | 0 |
| Separability | A | A | A | A | A | A | A | A | A |
| Transparency | S | S | S | S | S | S | S | S | S |
| Non-sticky feel | A | S | S | S | S | S | S | S | S |
| Gloss | S | A | A | A | B | A | A | A | B |
| Long-lasting gloss effect | S | A | A | A | B | A | A | A | B |

TABLE 5

| | Test Example | | | |
|---|---|---|---|---|
| | 3-9 | 3-10 | 3-11 | 3-12 |
| Hydrogenated polyisobutene (*2) | 38.5 | 28 | 10 | — |
| Vaseline (*14) | 31.5 | 42 | 55 | 70 |
| Diphenyl dimethicone (*3) | 30 | 30 | 30 | 30 |
| Ratio of hydrogenated polyisobutene in the non-volatile hydrocarbon oil | 55 | 40 | 15 | 0 |
| Separability | A | A | A | A |
| Transparency | S | A | A | B |
| Non-sticky feel | S | S | S | S |
| Gloss | S | A | A | B |
| Long-lasting gloss effect | A | A | A | B |

(*12): KAYDOL (manufactured by Central Tank Terminal Co., Ltd. Formerly Japan Vopak)
(*13): SYNCELANE 4 (manufactured by Nikko Chemicals Co., Ltd.)
(*14): VASELINE-E (manufactured by NIKKO RICA CORPORATION)

According to Tables 4 and 5, a tendency was observed that the long-lasting gloss effect is lower as the blending quantity of hydrogenated polyisobutene is smaller.

Accordingly, the blending quantity of hydrogenated polyisobutene is preferably 15% by mass or more, more preferably 40% by mass or more, and particularly preferably 55% by mass or more Next, the influence of an oily thickener on separability between the (a1) component and the (a2) component was examined.

The present inventors evaluated each sample shown in Table 6 below by the evaluation method (1) described above. The results are shown in Table 6.

TABLE 6

| | Test Example | | | | |
|---|---|---|---|---|---|
| | 4-1 | 4-2 | 4-3 | 4-4 | 4-5 |
| Hydrogenated polyisobutene (*2) | 70 | 70 | 70 | 70 | 70 |
| Diphenyl dimethicone (*3) | 30 | 30 | 30 | 30 | 30 |
| Dextrin palmitate (*15) | — | 0.1 | 1 | 5 | 10 |
| Separability | A | A | B | C | C |

(*15): Rheopearl KL (manufactured by Chiba Flour Milling Co., Ltd.)

As shown in Table 6, it was proved that as the blending quantity of the oily thickener in the oil phase increases, it influences separability between the (a1) component and the (a2) component.

Next, an examination was conducted on the case where a (a3) oily thickener was blended in practical oil-in-water emulsion lip cosmetics.

The present inventors prepared each sample (liquid lipstick) shown in Table 7 below in a usual manner and evaluated them by the evaluation method (3) described above. The results are shown in Table 7.

TABLE 7

| | | | Test Example | |
|---|---|---|---|---|
| | | | 5-1 | 5-2 |
| (A) | (a1) | Hydrogenated polyisobutene (*2) | 38.36 | 43.46 |
| | (a2) | Diphenyl dimethicone (*3) | 17.7 | 18.63 |
| | (a3) | Dextrin palmitate (*15) | 5 | — |
| (B) | (b1) | Ion exchanged water | balance | balance |
| | | Dipropylene glycol (*11) | 5 | 5 |
| | | Ethanol (*17) | 1.5 | 1.5 |
| | | Phenoxyethanol (*18) | 0.15 | 0.15 |
| | | Sodium dehydroacetate(*19) | 0.2 | 0.2 |
| | | Polyvinyl alcohol (*9) | 0.5 | 0.5 |
| | | Bentonite (*20) | 0.3 | 0.3 |
| | (b2) | Red No. 227 | 0.1 | 0.1 |
| | | Behenyl alcohol (*21) | 1 | 1 |

TABLE 7-continued

| | | Test Example | |
|---|---|---|---|
| | | 5-1 | 5-2 |
| (C) | Sorbitan monostearate (*8) | 1 | 1 |
| | Polysorbate 60 (*22) | 1 | 1 |
| | Sucrose fatty acid ester (*7) | 2.5 | 2.5 |
| | Long-lasting gloss effect | C | S |

(*17): SYNTHETIC ALCOHOL 99 DEGREE OF ALCOHOLICITY (manufactured by JAPAN SYNTHETIC ALCOHOL CO., Ltd.)
(*18): HISOLVE EPH (manufactured by TOHO Chemical Industry Co., Ltd.)
(*19): SODIUM METAPHOSPHATE (manufactured by KOKUSAN CHEMICAL Co., Ltd.)
(*20): BENTONE 38VCG (manufactured by Elementis pic)
(*21): BEHENYL ALCOHOL 65 (manufactured by Nikko Chemicals Co., Ltd.)
(*22): NIKKOLTS-10V (manufactured by NIPPON SURFACTANT INDUSTRIES CO., LTD.)

According to the Test Example 5-1, it was found that the long-lasting gloss effect is decreased when a large amount of the oily thickener is blended into the oil-in-water emulsion lip cosmetic. This is because, as shown in Table 6, the oily thickener has impaired the separability between the (a1) component and the (a2) component.

In contrast, the oil-in-water emulsion lip cosmetic of the Test Example 5-2, which contained no oily thickener, was excellent in watery feel, gloss, long-lasting gloss and transparency.

Accordingly, it is necessary that the oil-in-water emulsion lip cosmetic of the present invention comprises an oil phase containing a (a1) non-volatile hydrocarbon oil containing hydrogenated polyisobutene and (a2) methylphenyl silicone which separates out when mixed with (a1) at 25° C.; and an aqueous phase containing an (b1) aqueous component and a (b2) colorant Furthermore, as a result of Tables 6 and 7 and the present inventors' examination, in the oil-in-water emulsion cosmetics of the present invention, it was found that when the (a3) oily thickener is blended into the cosmetics, the blending quantity is preferably 1% by mass or less, preferably less than 0.1% by mass, and particularly preferably the thickener is not included.

Next, for an oil-in-water emulsion lip cosmetic, examinations were conducted on the blending quantity of a water-soluble thickener and to which phase a higher alcohol should be added, if it is added.

The present inventors prepared each sample (liquid lipstick) shown in Table 8 below in a usual manner and evaluated them by the evaluation method (4) described above. The results are shown in Table 8.

TABLE 8

| | | | Test Example | | | |
|---|---|---|---|---|---|---|
| | | | 6-1 | 6-2 | 6-3 | 6-4 |
| (A) | (a1) | Hydrogenated polyisobutene (*2) | 43.46 | 43.46 | 43.46 | 43.46 |
| | (a2) | Diphenyl dimethicone (*3) | 18.63 | 18.63 | 18.63 | 18.63 |
| (B) | (b1) | Ion exchanged water | balance | balance | balance | balance |
| | | Dipropylene glycol (*11) | 5 | 5 | 5 | 5 |
| | | Ethanol (*17) | 1.5 | 1.5 | 1.5 | 1.5 |
| | | Phenoxyethanol (*18) | 0.15 | 0.15 | 0.15 | 0.15 |
| | | Sodium dehydroacetate (*19) | 0.2 | 0.2 | 0.2 | 0.2 |
| | | Sodium metaphosphate (*23) | 0.05 | 0.05 | 0.05 | 0.05 |

TABLE 8-continued

|  |  | Test Example | | | |
|---|---|---|---|---|---|
|  |  | 6-1 | 6-2 | 6-3 | 6-4 |
|  | Polyvinyl alcohol (*9) | 1 | 1 | 0.5 | 0.5 |
|  | Bentonite (*20) | 0.6 | 0.3 | 0.3 | 0.3 |
| (b2) | Red No. 202 | 1 | 1 | 1 | 1 |
|  | Behenyl alcohol (*21) | — | — | 1 | 1 |
|  | Sorbitan monostearate (*8) | 1 | 1 | 1 | 1 |
|  | Polysorbate 60 (*22) | 1 | 1 | 1 | 1 |
|  | Sucrose fatty acid ester (*7) | 2.5 | 2.5 | 2.5 | 2.5 |
| Which phase a higher alcohol is added | | — | — | Oil phase | Water phase |
| Stability at high temperatures | | A | C | B | A |

(*23): SODIUM METAPHOSPHATE (manufactured by KOKUSAN CHEMICAL Co., Ltd.)

It was found that when the water-soluble thickener was blended in a large amount, specifically 0.6% by mass or more, the sample was excellent in stability at high temperatures (Test Example 6-1).

It was also found that even if the water-soluble thickener was not blended in a large amount, the sample was excellent in stability at high temperatures when a higher alcohol was added to the aqueous phase (Test Example 6-4).

In contrast, it was found that when a higher alcohol was added to the oil phase, the sample's stability at high temperatures is slightly inferior to that of the example with the addition of a higher alcohol to its aqueous phase (Test Example 6-3).

Therefore, in the oil-in-water emulsion lip cosmetic of the invention of the present application, when a higher alcohol is blended into the cosmetic, it is preferably added to the (B) aqueous phase.

Next, for an oil-in-water emulsion lip cosmetic, an examination was conducted on to which phase the (b2) colorant should be added.

The present inventors prepared each sample (liquid lipstick) shown in Table 9 below in a usual manner and evaluated them by the evaluation method (2) described above. Another evaluation was conducted on the transparency of the (A) phase based on the evaluation method (5) described above. The results are shown in Table 9.

TABLE 9

|  |  |  | Test Example | |
|---|---|---|---|---|
|  |  |  | 7-1 | 7-2 |
| (A) | (a1) | Hydrogenated polyisobutene (*2) | 43.46 | 43.46 |
|  | (a2) | Diphenyl dimethicone (*3) | 18.63 | 18.63 |

TABLE 9-continued

|  |  |  | Test Example | |
|---|---|---|---|---|
|  |  |  | 7-1 | 7-2 |
| (B) | (b1) | Ion exchanged water | balance | balance |
|  |  | Dipropylene glycol (*11) | 5 | 5 |
|  |  | Ethanol (*17) | 1.5 | 1.5 |
|  |  | Phenoxyethanol (*18) | 0.15 | 0.15 |
|  |  | Sodium dehydroacetate (*19) | 0.2 | 0.2 |
|  |  | Sodium metaphosphate (*23) | 0.05 | 0.05 |
|  |  | Polyvinyl alcohol (*9) | 0.5 | 0.5 |
|  |  | Bentonite (*20) | 0.3 | 0.3 |
| (b2) | | Red No. 202 | 1 | 1 |
|  | | Behenyl alcohol (*21) | 1 | 1 |
|  | | Sorbitan monostearate (*8) | 1 | 1 |
|  | | Polysorbate 60 (*22) | 1 | 1 |
|  | | Sucrose fatty acid ester (*7) | 2.5 | 2.5 |
| Which phase a (b2) component is added | | | Oil phase | Water phase |
| Transparency of (A) phase | | | C | A |
| Color difference between the appearance of the sample and the lips after application | | | C | A |

It was found that when the (b2) colorant was added to the aqueous phase, a color difference between the sample appearance and the lips after application is small and the transparency of gloss was high (Test Example 7-2). In contrast, it was found that when the colorant was added to the oil phase, a color difference between the sample appearance and the lips after application increased (Test Example 7-1).

Hereinafter, Formulation Examples of the oil-in-water emulsion lip cosmetic of the present invention will be illustrated (formulation examples 1 to 12: liquid lipstick, formulation example 13: solid lipstick). The present invention is not limited by these Formulation Examples.

TABLE 10

|  |  |  | Formulation Example | | | | | | |
|---|---|---|---|---|---|---|---|---|---|
|  |  |  | 1 | 2 | 3 | 4 | 5 | 6 | 7 |
| (A) | (a1) | Hydrogenated polyisobutene (*2) | 5 | 25 | 25 | 24 | 19 | 29 | 25 |
|  |  | Vaseline (*14) | — | 30 | — | 10 | — | — | 5 |
|  |  | Liquid paraffin (*12) | — | — | 29 | — | — | — | — |
|  |  | Microcrystalline wax (*24) | — | — | 1 | — | — | — | — |
|  | (a2) | Diphenyl dimethicone (*3) | 5 | 13 | 13 | 23 | 18 | 33 | 18 |
|  |  | Di(phytosteryl/octyldodecyl) lauroylglutamate (*25) | — | — | — | 10 | — | — | — |
|  |  | Dimer dilinolic acid di(phytosteryl/behenyl) (*26) | — | — | — | — | 20 | — | 10 |
|  |  | Diisostearyl malate (*27) | — | — | — | — | — | 3 | — |
| (B) | (b1) | Ion exchanged water | balance | balance | balance | balance | balance | balance | balance |
|  |  | Dipropylene glycol (*11) | 5 | 5 | 5 | 5 | 5 | 5 | 5 |
|  |  | 1.3-butylene glycol (*28) | — | — | — | — | — | — | — |

TABLE 10-continued

|  |  | Formulation Example | | | | | | |
|---|---|---|---|---|---|---|---|---|
|  |  | 1 | 2 | 3 | 4 | 5 | 6 | 7 |
|  | Ethanol (*17) | 1.5 | 1.5 | 1.5 | 1.5 | 1.5 | 1.5 | 1.5 |
|  | Phenoxyethanol (*18) | 0.2 | 0.2 | 0.2 | 0.2 | 0.2 | 0.2 | 0.2 |
|  | Sodium dehydroacetate (*19) | 0.2 | 0.2 | 0.2 | 0.2 | 0.2 | 0.2 | 0.2 |
|  | Sodium metaphosphate (*23) | 0.05 | 0.05 | 0.05 | 0.05 | 0.05 | 0.05 | 0.05 |
|  | Polyvinyl alcohol (*9) | 0.5 | 0.5 | 0.5 | 0.5 | 0.5 | 0.5 | 0.5 |
|  | Bentonite (*20) | 0.3 | 0.3 | 0.3 | 0.3 | 0.3 | 0.3 | 0.3 |
| (b2) | Red No. 202 | 1 | — | 1 | 1 | — | 1 | 10 |
|  | Red No. 201 | — | — | — | — | 10 | — | — |
|  | Red No. 207 | — | 1 | — | — | — | — | — |
|  | Titanium oxide | — | — | 1 | — | — | — | — |
|  | Behenyl alcohol (*21) | 1 | 2 | 1 | 0.5 | — | — | 1 |
|  | Stearyl alcohol (*33) | — | — | — | — | — | 1 | — |
|  | Cetanol (*34) | — | — | — | — | — | — | — |
|  | Sorbitan monostearate (*8) | 1 | 2 | 1 | 1 | 1 | 1 | — |
|  | Polysorbate 60 (*22) | 1 | — | — | 5 | 1.5 | 0.5 | — |
|  | PEG-40 stearate (*35) | — | 1 | — | — | — | — | — |
|  | Beheneth-20 (*36) | — | — | 2 | — | — | — | — |
|  | Glyceryl stearate (SE) (*37) | — | — | — | — | — | — | 1 |
|  | Sucrose fatty acid ester (*7) | 2.5 | 3 | 1 | — | 2.5 | 3 | 3 |

TABLE 11

|  |  |  | Formulation Example | | | | | |
|---|---|---|---|---|---|---|---|---|
|  |  |  | 8 | 9 | 10 | 11 | 12 | 13 |
| (A) | (a1) | Hydrogenated polyisobutene (*2) | 35 | 55 | 15 | 40 | 40 | 38 |
|  |  | Vaseline (*14) | — | — | — | — | — | 10 |
|  | (a2) | Diphenyl dimethicone (*3) | 13 | 5 | 5 | 20 | 20 | 20 |
|  |  | Trimethyl pentaphenyl trisiloxane (*4) | 10 | — | — | — | — | — |
|  |  | Polyglyceryl-10 (behenate/eicosadioate) (*32) | — | — | — | — | — | 3 |
|  |  | Dimer dilinolic acid di(phytosteryl/behenyl) (*26) | — | — | — | — | — | 10 |
| (B) | (b1) | Ion exchanged water | balance | balance | balance | balance | balance | balance |
|  |  | Dipropylene glycol (*11) | 5 | 5 | 5 | 5 | 5 | — |
|  |  | 1.3-butylene glycol (*28) | — | — | — | — | — | 5 |
|  |  | Ethanol (*17) | 1.5 | 1.5 | 1.5 | 1.5 | 1.5 | 1.5 |
|  |  | Phenoxyethanol (*18) | 0.2 | 0.2 | 0.2 | 0.2 | 0.2 | 0.2 |
|  |  | Sodium dehydroacetate (*19) | 0.2 | 0.2 | 0.2 | 0.2 | 0.2 | 0.2 |
|  |  | Sodium metaphosphate (*23) | 0.05 | 0.05 | 0.05 | 0.05 | 0.05 | 0.05 |
|  |  | Polyvinyl alcohol (*9) | 0.5 | 0.5 | 0.5 | 0.5 | 0.5 | 0.5 |
|  |  | Bentonite (*20) | 0.3 | — | — | — | — | 0.3 |
|  |  | Xanthane gum (*28) | — | 0.05 | — | — | — | — |
|  |  | (PEG-240/decyltetradeceth-20/HDI) copolymer (*30) | — | — | 2 | — | — | — |
|  |  | Hydroxyl propyl methyl cellulose stearoxy ether (*31) | — | — | — | 1 | 1 | — |
|  | (b2) | Red No. 202 | — | 1 | 1 | 1 | 0.1 | 1 |
|  |  | Titanium oxide | 10 | — | — | — | — | — |
|  |  | Behenyl alcohol (*21) | — | 1 | 1 | 1 | 1 | 1 |
|  |  | Cetanol (*34) | 2 | — | — | — | — | — |
|  |  | Sorbitan monostearate (*8) | 1 | 1 | 2 | 1 | 1 | 1 |
|  |  | Polysorbate 60 (*22) | — | — | 3 | 3 | 1 | 1 |
|  |  | Beheneth-20 (*36) | — | — | 1 | — | — | — |
|  |  | Sorbitan sesquiisostearate (*38) | 0.5 | — | — | — | — | — |
|  |  | PEG-5 glyceryl stearate (*39) | — | 2 | — | — | — | — |
|  |  | Sucrose fatty acid ester (*7) | — | 3 | 3 | 2 | 3 | 3 |

(*24): Microcrystalline wax P (manufactured by NIKKO RICA CORPORATION)
(*25): ELDEW PS-203R (manufactured by AJINOMOTO CO., INC.)
(*26): LUSPLAN PI-DA (manufactured by Nippon Fine Chemical)
(*27): COSMOL 222(S) (manufactured by The Nisshin OilliO Group, Ltd.)
(*28): 1.3-butylene glycol (manufactured by Daicel Corporation.)
(*29): KELTROLT (manufactured by CP Kelco)
(*30): ADEKA NOL GT-700 (manufactured by ADEKA CORPORATION)
(*31): Sangelose 90L (manufactured by DAIDO CHEMICAL CORPORATION)
(*32): NOMCORT HK-P (manufactured by The Nisshin OilliO Group, Ltd.)
(*33): Stearyl alcohol NX (manufactured by KOKYU ALCOHOL KOGYO CO., LTD.)
(*34): CONOL 30RC (manufactured by New Japan Chemical Co., Ltd.)
(*35): MYS-40V (manufactured by NIPPON SURFACTANT INDUSTRIES CO., LTD.)
(*36): NIKKOL BB-20 (manufactured by NIPPON SURFACTANT INDUSTRIES CO., LTD.)

(*37): NIKKOL Tegin TV (manufactured by NIPPON SURFACTANT INDUSTRIES CO., LTD.)
(*38): ESTEMOL 182 V (manufactured by The Nisshin OilliO Group, Ltd.)
(*39): EMALEX GM-5 (manufactured by NIHON EMULSION Co., Ltd.)

What is claimed is:

1. An oil-in-water emulsion lip cosmetic, comprising:
   (A) an oil phase comprising (a1) and (a2), wherein:
      (a1) is 5 to 70% by mass, relative to the total mass of the cosmetic, of a non-volatile hydrocarbon oil including hydrogenated polyisobutene; and
      (a2) is 5 to 70% by mass, relative to the total mass of the cosmetic, of methylphenyl silicone that separates from (a1) when (a1) and (a2) are mixed with at 25° C.; and
   (B) an aqueous phase comprising (b1) and (b2), wherein:
      (b1) is 10 to 80% by mass, relative to the total mass of the cosmetic, of an aqueous component; and
      (b2) is 0.01 to 10% by mass, relative to the total mass of the cosmetic, of a colorant.

2. The oil-in-water emulsion lip cosmetic, according to claim 1, further comprising:
   an (a3) oil-soluble thickener in said (A) oil phase; and
   wherein a blending quantity of said oil-soluble thickener is at most 1% by mass in the cosmetic.

3. The oil-in-water emulsion lip cosmetic, according to claim 2, wherein:
   a blending quantity of said hydrogenated polyisobutene is at least 15% by mass of the non-volatile hydrocarbon oil.

4. The oil-in-water emulsion lip cosmetic, according to claim 2, wherein:
   said (a2) methylphenyl silicone is one silicon derivative selected from a group consisting of diphenyl dimethicone and trimethyl pentaphenyl trisiloxane.

5. The oil-in-water emulsion lip cosmetic, according to claim 2, wherein:
   said (b2) colorant comprises a water-soluble dye.

6. The oil-in-water emulsion lip cosmetic, according to claim 2, wherein:
   said cosmetic comprises at least one component selected from a group consisting of a hydrophilic polymer and a hydrophilic surfactant, and said (b2) component comprises an organic pigment.

7. The oil-in-water emulsion lip cosmetic, according to claim 2, wherein:
   the (b1) aqueous component further comprises a higher alcohol.

8. The oil-in-water emulsion lip cosmetic, according to claim 1, wherein:
   a blending quantity of said hydrogenated polyisobutene is at least 15% by mass of the non-volatile hydrocarbon oil.

9. The oil-in-water emulsion lip cosmetic, according to claim 8, wherein:
   said (a2) methylphenyl silicone is one silicon derivative selected from a group consisting of diphenyl dimethicone and trimethyl pentaphenyl trisiloxane.

10. The oil-in-water emulsion lip cosmetic, according to claim 8, wherein:
    said (b2) colorant comprises a water-soluble dye.

11. The oil-in-water emulsion lip cosmetic, according to claim 8, wherein:
    said cosmetic comprises at least one component selected from a group consisting of a hydrophilic polymer and a hydrophilic surfactant, and said (b2) component comprises an organic pigment.

12. The oil-in-water emulsion lip cosmetic, according to claim 8, wherein:
    the (b1) aqueous component further comprises a higher alcohol.

13. The oil-in-water emulsion lip cosmetic, according to claim 1, wherein:
    said (a2) methylphenyl silicone is one silicon derivative selected from a group consisting of diphenyl dimethicone and trimethyl pentaphenyl trisiloxane.

14. The oil-in-water emulsion lip cosmetic, according to claim 13, wherein:
    said (b2) colorant comprises a water-soluble dye.

15. The oil-in-water emulsion lip cosmetic, according to claim 13, wherein:
    said cosmetic comprises at least one component selected from a group consisting of a hydrophilic polymer and a hydrophilic surfactant, and said (b2) component comprises an organic pigment.

16. The oil-in-water emulsion lip cosmetic, according to claim 1, wherein:
    said (b2) colorant comprises a water-soluble dye.

17. The oil-in-water emulsion lip cosmetic, according to claim 16, wherein:
    said cosmetic comprises at least one component selected from a group consisting of a hydrophilic polymer and a hydrophilic surfactant, and said (b2) component comprises an organic pigment.

18. The oil-in-water emulsion lip cosmetic, according to claim 1, wherein:
    said cosmetic comprises at least one component selected from a group consisting of a hydrophilic polymer and a hydrophilic surfactant, and said (b2) component comprises an organic pigment.

19. The oil-in-water emulsion lip cosmetic, according to claim 1, wherein:
    the (b1) aqueous component further comprises a higher alcohol.

* * * * *